(12) United States Patent
Leung

(10) Patent No.: US 8,216,284 B2
(45) Date of Patent: *Jul. 10, 2012

(54) BONE FIXATION ASSEMBLY

(75) Inventor: Takkwong Ross Leung, Piscataway, NJ (US)

(73) Assignee: EBI, LLC, Parsippany, NJ (US)

( * ) Notice: Subject to any disclaimer, the term of this patent is extended or adjusted under 35 U.S.C. 154(b) by 168 days.

This patent is subject to a terminal disclaimer.

(21) Appl. No.: 12/713,222

(22) Filed: Feb. 26, 2010

(65) Prior Publication Data

US 2010/0160973 A1    Jun. 24, 2010

Related U.S. Application Data

(63) Continuation of application No. 11/124,535, filed on May 5, 2005, now Pat. No. 7,766,948.

(51) Int. Cl.
*A61B 17/04*    (2006.01)

(52) U.S. Cl. .................................................. 606/289

(58) Field of Classification Search .................. 606/280, 606/289, 291, 305, 315, 316, 319; 411/166, 411/187, 188, 399
See application file for complete search history.

(56) References Cited

U.S. PATENT DOCUMENTS

| | | | |
|---|---|---|---|
| 5,205,694 A | 4/1993 | Nagoshi et al. | |
| 5,275,601 A * | 1/1994 | Gogolewski et al. | 606/291 |
| 5,456,719 A | 10/1995 | Keller | |
| 5,601,553 A | 2/1997 | Trebing et al. | |
| 5,607,426 A | 3/1997 | Ralph et al. | |
| 5,709,686 A | 1/1998 | Talos et al. | |
| 5,772,376 A | 6/1998 | Konig | |
| 6,206,881 B1 | 3/2001 | Frigg et al. | |
| 6,361,537 B1 | 3/2002 | Anderson | |
| 6,572,622 B1 | 6/2003 | Schäfer et al. | |
| 6,599,290 B2 | 7/2003 | Bailey et al. | |
| 6,610,062 B2 | 8/2003 | Bailey et al. | |
| 6,623,486 B1 | 9/2003 | Weaver et al. | |
| 6,716,214 B1 | 4/2004 | Jackson | |
| 6,730,091 B1 | 5/2004 | Pfefferle | |
| 7,175,624 B2 | 2/2007 | Konieczynski et al. | |
| 7,229,442 B2 | 6/2007 | Schafer | |
| 2003/0225409 A1 | 12/2003 | Freid et al. | |
| 2004/0073218 A1 | 4/2004 | Dahners | |
| 2004/0127896 A1 | 7/2004 | Lombardo et al. | |
| 2005/0096657 A1 | 5/2005 | Autericque et al. | |
| 2005/0101961 A1 | 5/2005 | Huebner et al. | |
| 2005/0165400 A1 | 7/2005 | Fernandez | |
| 2006/0004362 A1 | 1/2006 | Patterson et al. | |

* cited by examiner

*Primary Examiner* — Eduardo C Robert
*Assistant Examiner* — Tara Carter
(74) *Attorney, Agent, or Firm* — Harness, Dickey

(57) ABSTRACT

A bone fixation assembly is provided and may include a fixation member defining at least one aperture. At least two locking features may be circumferentially spaced around an inner perimeter of the at least one aperture and may include a first end and a second end. The at least two locking features may each include a longitudinal axis extending substantially perpendicular to an axis extending through the at least one aperture. A fastener may include at least two discrete locking members respectively received in the at least two locking features at the first end. The at least two discrete locking members may be circumferentially spaced around an outer perimeter of the fastener, may extend from an outer surface of a head of the fastener, and may be received within the first end in an unlocked state and rotated from the first end to the second end in a locked state.

18 Claims, 6 Drawing Sheets

BONE FIXATION ASSEMBLY

CROSS-REFERENCE TO RELATED APPLICATIONS

This application is a continuation of U.S. patent application Ser. No. 11/124,535 filed on May 5, 2005. The entire disclosure of the above application is incorporated herein by reference.

INTRODUCTION

In certain orthopedic surgical procedures, it is necessary to secure multiple bones or bone portions relative to each other. For example, in spinal surgeries, the fusion of two or more vertebral bodies is required to secure a portion of the spinal column in a desired position. Portions of other bones of the human body can be similarly joined. This need may be the result of physical trauma from fractures or dislocations, degenerative diseases, or tumors.

Various plating systems for internal fixation of various bones are known. Such systems generally include a plate that is attached to the bone or bone portions spanning a fracture line or a spinal disk space. The plate typically includes a plurality of holes through which bone screws are inserted for engaging the bone.

Some plating systems include constrained or locking screws, which are adapted for locking in corresponding plate holes in a fixed orientation. Other plating systems include semi-constrained or non-locking screws, which can be configured to maintain a variable orientation relative to the plate. An example of a plating system that includes constrained and semi-constrained screws is disclosed in currently pending, co-owned U.S. patent application Ser. No. 11/023,096, filed Dec. 22, 2004, the contents of which are incorporated herein by reference. A plating system that includes a locking ring that prevents the screw from backing out of the plate is disclosed in co-owned U.S. Pat. No. 6,599,290, the contents of which are incorporated herein by reference.

Although the existing plating systems can be satisfactory for their intended purposes, there is still a need for new plating systems that are effective and efficient and also provide operative simplicity and versatility to the surgeon.

SUMMARY

A bone fixation assembly is provided and may include a fixation member defining at least one aperture formed through the fixation member. At least two locking features may be circumferentially spaced around an inner perimeter of the at least one aperture and may include a first end and a second end. The at least two locking features may each include a longitudinal axis extending substantially perpendicular to an axis extending through the at least one aperture. A fastener may be received within the at least one aperture and may include at least two discrete locking members respectively received in the at least two locking features at the first end. The at least two discrete locking members may be circumferentially spaced around an outer perimeter of the fastener, may extend from an outer surface of a head of the fastener, and may be received within the first end in an unlocked state and rotated from the first end to the second end in a locked state to restrict removal of the fastener from the at least one aperture.

In another configuration, a bone fixation assembly is provided and may include a bone plate for positioning relative to a bone. The bone plate may define an aperture extending therethrough and at least two locking features each having a first end and a second end. A bone fastener may be rotatable relative to the bone plate and may include a shaft extending through the aperture, a head positioned in the aperture, and at least two discrete locking members extending from an outer surface of the head and received in the first end of respective ones of the at least two locking features in a direction substantially parallel to a longitudinal axis of the fastener. The bone fastener and the at least two discrete locking members may be rotatable relative to the bone plate from the first end to the second end. The second end may engage respective ones of the at least two discrete locking members in a direction substantially parallel to an axis extending through the aperture to secure the bone plate and the fastener to the bone.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, the present teachings can be used for, but are not limited to, fusion procedures of adjoining bones, such as vertebrae, and/or for internal fixation of fractures in any bones.

Figure 1:
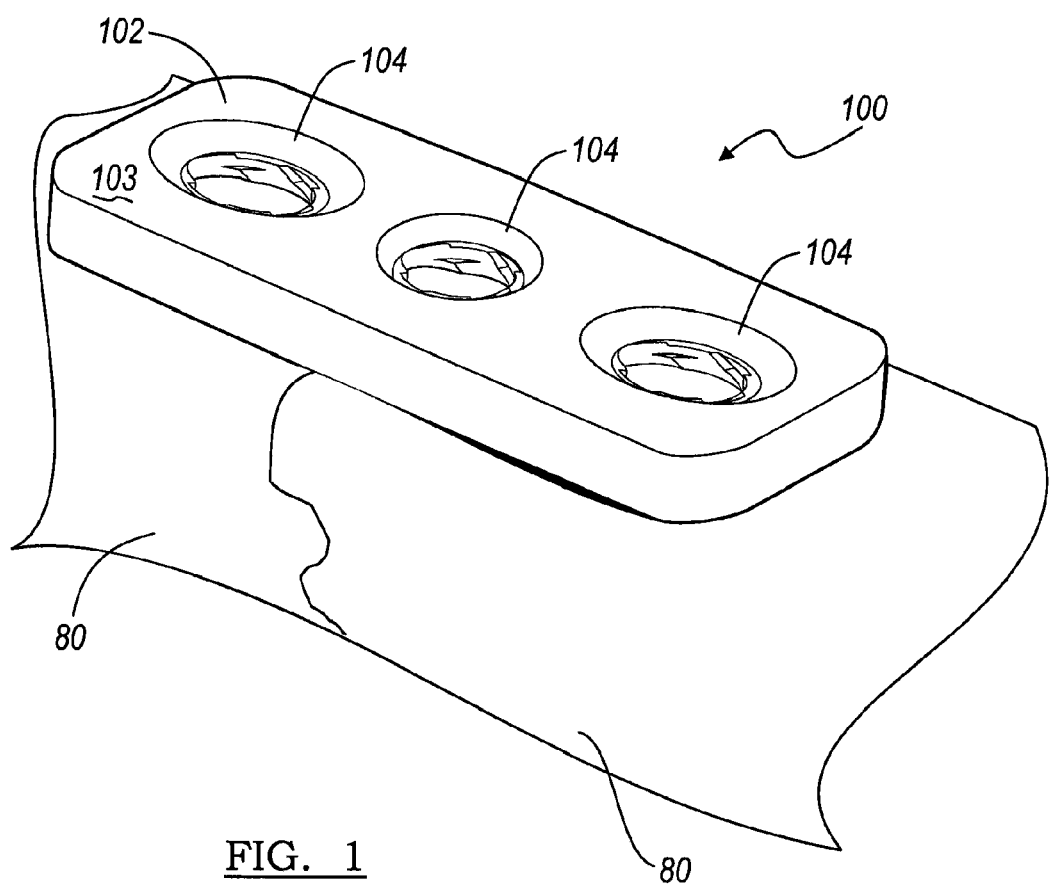
FIG. 1 is an environmental and perspective view of a bone fixation assembly according to the present teachings, the bone fixation assembly shown operatively associated with a bone.
Figure 2:
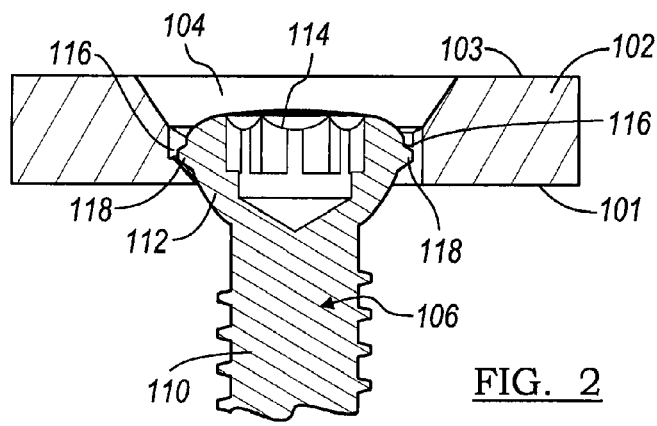
FIG. 2 is a sectional view of a bone fixation assembly illustrating a locking fastener according to the present teachings.
Figure 3:
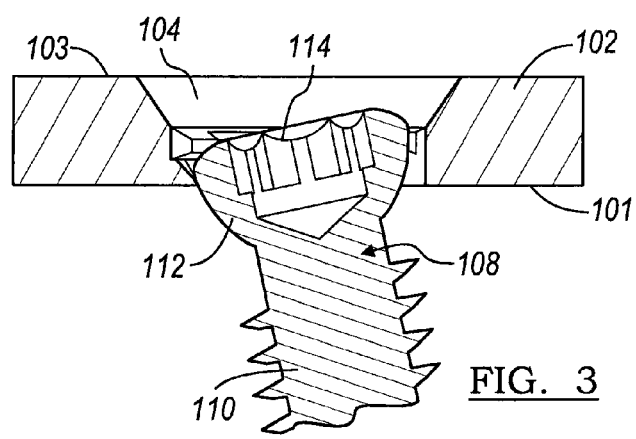
FIG. 3 is a sectional view similar to FIG. 2 illustrating a non-locking fastener according to the present teachings.
Figure 4:
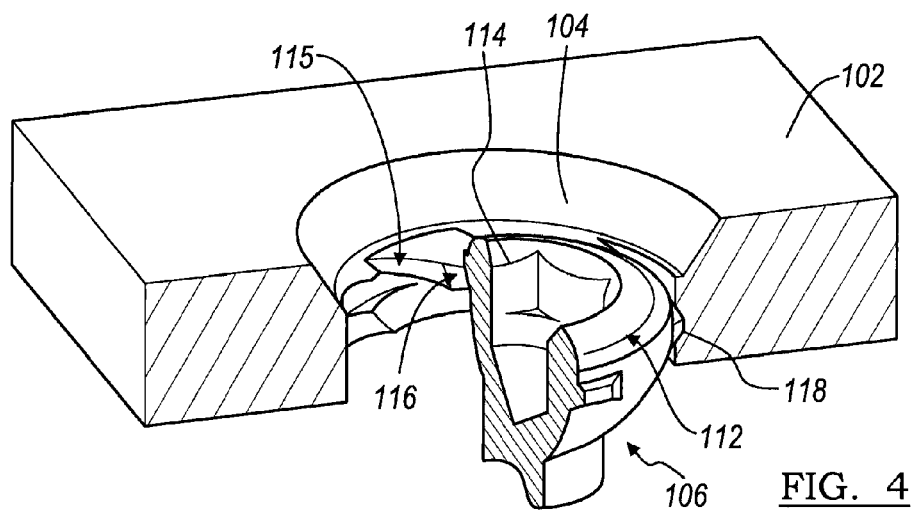
FIG. 4 is a partially cut-away perspective view of a bone fixation assembly illustrating a locking fastener according to the present teachings.
Figure 5:
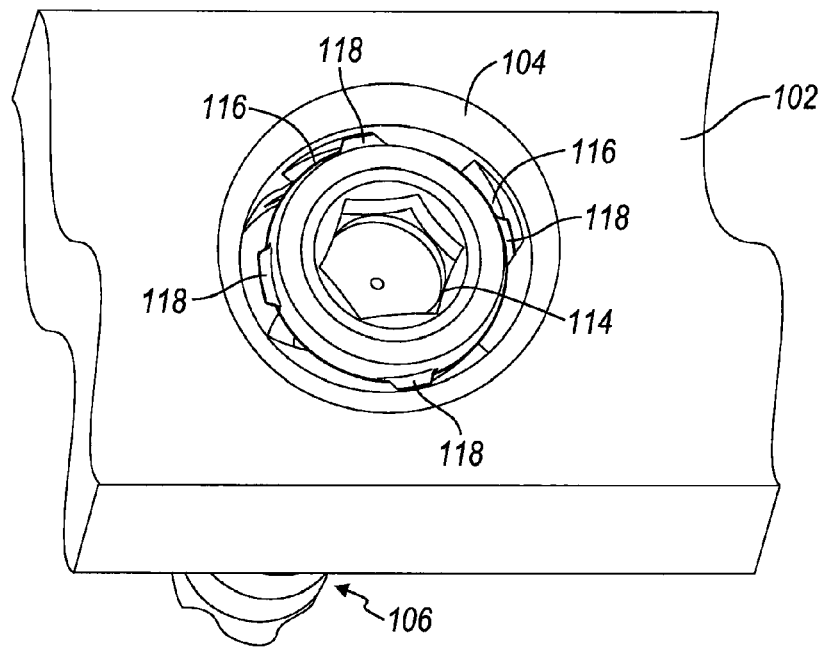
FIG. 5 is a top perspective view of a bone fixation assembly with a locking fastener according to the present teachings.

Referring to FIG. 1, an exemplary bone fixation assembly 100 according to the present teachings is illustrated in internal fixation of two bones or bone portions 80. Referring to FIGS. 1-3, the bone fixation assembly 100 includes a fixation member 102 that has a bone engagement surface 101 and an opposite, non-engagement surface 103. The fixation member 102 can be a substantially planar plate or planar bar, or can be a substantially curved shell that has an anatomically adapted shape. The fixation member 102 has generally a dimension spanning the opposing surfaces 101, 103 ("thickness"), such that the thickness of the fixation member 102 is substantially smaller than at least another dimension of the fixation member 102, such as a width or length of the fixation member 102. The thickness of the fixation member 102 can be variable.

The fixation member 102 can have one or more apertures 104 therethrough. At least one aperture 104 can be adapted for receiving selectively a locking fastener 106 or a non-locking fastener 108. Further, any of the apertures 104 can be adapted for compression locking, as will be discussed below in connection with FIGS. 9-12. Each of the locking and non-locking fasteners 106, 108 can include a shaft 110 and a head 112 integrally or modularly connected with the shaft 110. The shaft 110 can include a threaded portion for bone engagement and a head formation 114, such as a hex formation, for example. The head formation 114 is adapted for engagement with a driver or other insertion or extraction tool (not shown) in a conventional manner.

Referring to FIGS. 2, 4, 5, 7 and 8, the aperture 104 can include a non-threadable locking mechanism 115. The non-threadable locking mechanism 115 can include, for example, one or more locking grooves 116 configured for locking engagement with corresponding locking tabs 118 that extend from the head 112 of the locking fastener 106. Each locking groove 116 can have variable radius. In one aspect, the radius of the locking groove 116 decreases clockwise (as viewed from the non-engagement surface 103), such that clockwise rotation of the locking fastener 106 relative to the fixation member 102 guides the locking tabs 118 into locking engagement with the corresponding locking grooves 116 and locks the locking fastener 106 relative to the fixation member 102. The locking tabs 118 can be tightly engaged with the locking grooves 116 for preventing back-out of the locking fasteners 106. Although four locking grooves 116 and tabs 118 are illustrated herein, it will be appreciated that a different number of locking grooves 116 and tabs 118 can be used. Four locking grooves 116 and tabs 118, for example, may provide greater degree of locking stability relative to a lesser number.

In the locked position illustrated in FIG. 2, the shaft of the locking fastener 106 can be oriented substantially perpendicularly to the engagement surface 101. It will be appreciated, however, that locking fastener 106 can be retained in an unlocked position, in which the tabs 118 are not engaged with the locking grooves 116, such that the shaft 110 of the locking fastener 106 can angulate relative to the engagement surface 101 within a cone of angulation which is determinable by the specific dimensions and geometry of the aperture 104 and the locking fastener 106. In one application, the cone of angulation defines an angle of approximately 18° from an axis perpendicular to the fixation member 102.

Figure 6:
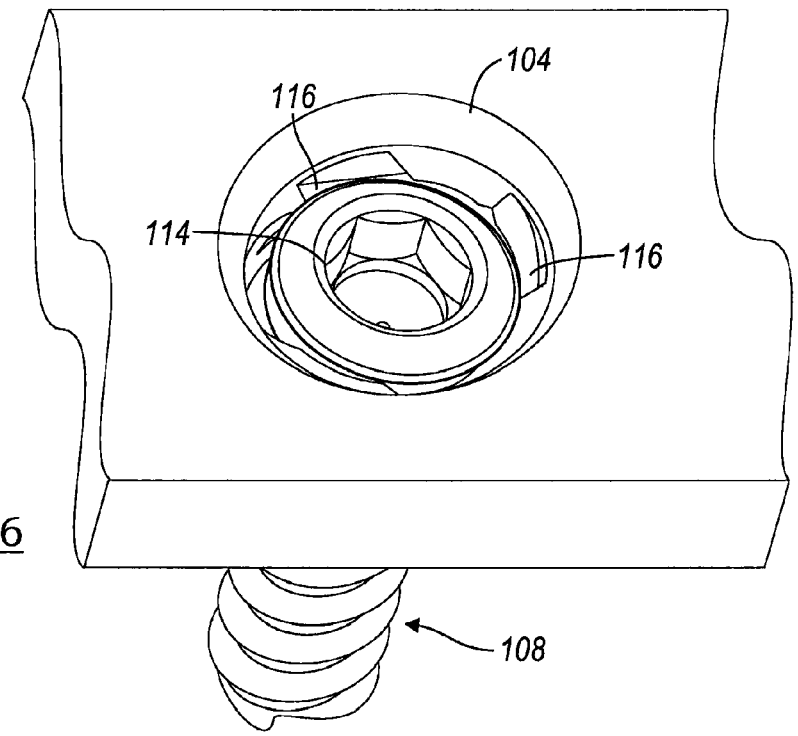
FIG. 6 is a perspective view of a bone fixation assembly illustrating a non-locking fastener according to the present teachings.
Figure 7:
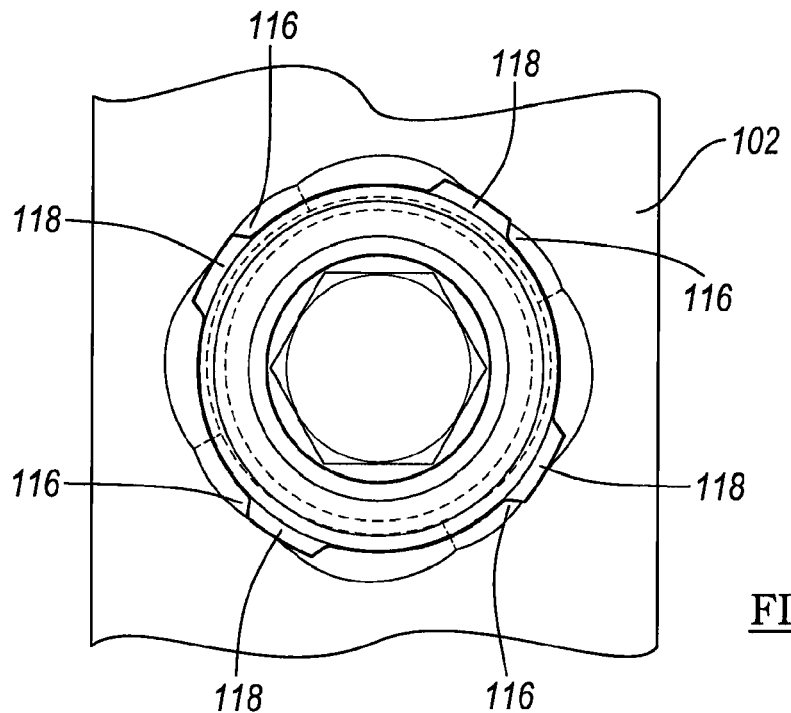
FIG. 7 is a top view of a bone fixation assembly illustrating a locking fastener according to the present teachings.
Figure 8:
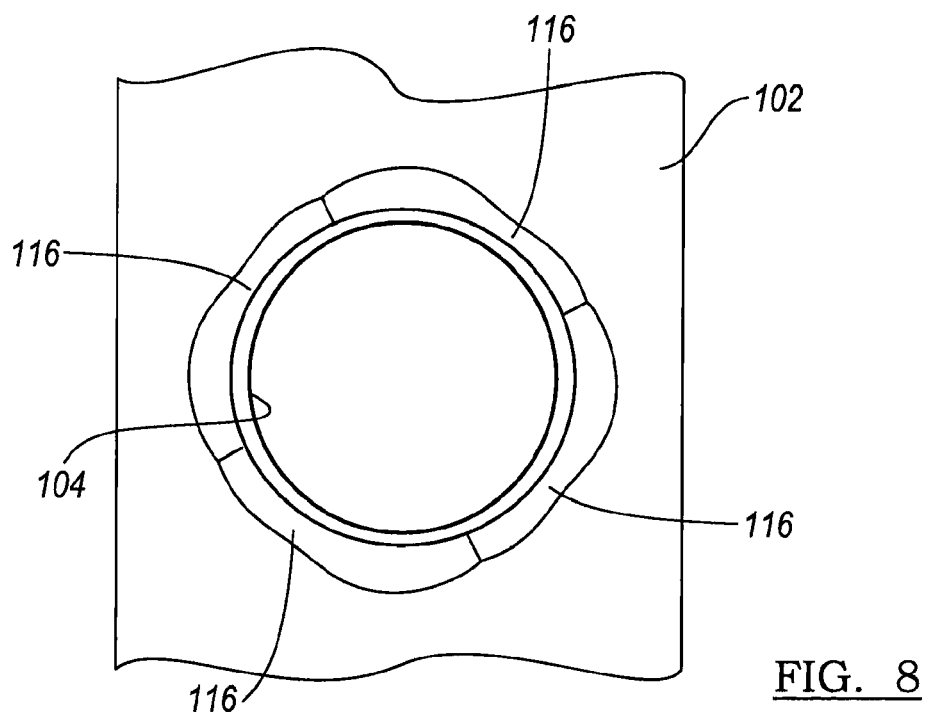
FIG. 8 is a top view of a bone fixation assembly illustrating an aperture according to the present teachings.

Referring to FIGS. 3 and 6, the non-locking fastener 108 can be received in the same aperture 104. The shaft 110 of the non-locking fastener 108 can angulate relative to the engagement surface 101 within a cone of angulation which is also determinable by the specific dimensions and geometry of the aperture 104 and the non-locking fastener 108.

Figure 9:
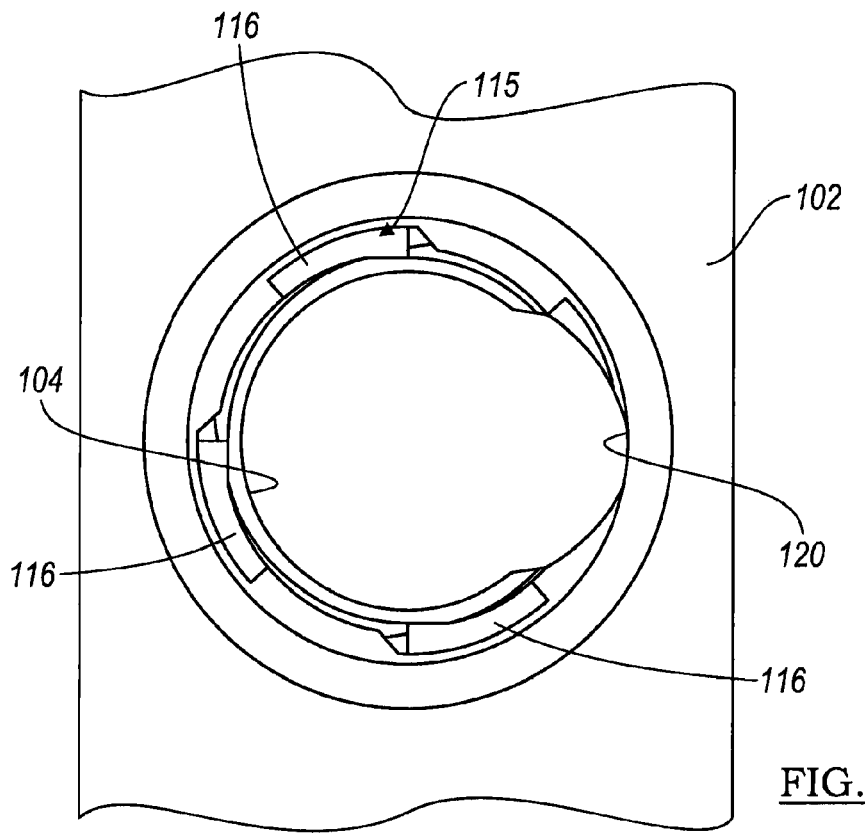
FIG. 9 is a plan view of a bone fixation assembly illustrating an aperture with a compression feature according to the present teachings.
Figure 10:
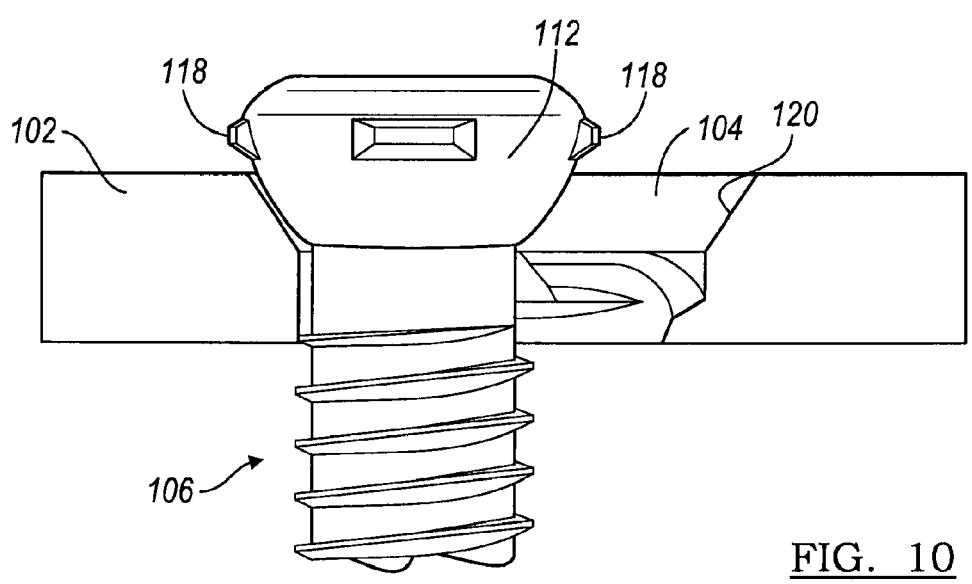
FIGS. 10-12 illustrate stages in a compression and locking procedure for a fixation assembly according to the present teachings.
Figure 11:
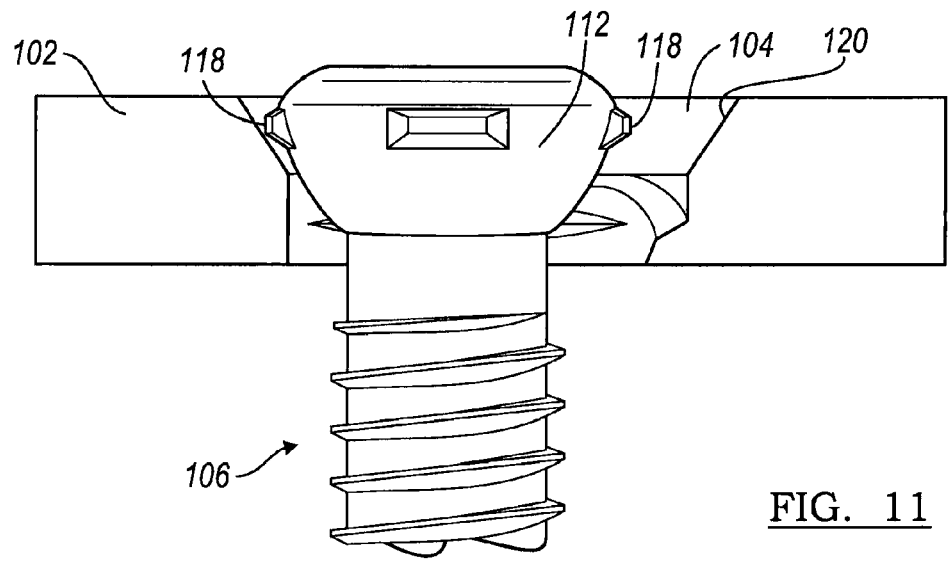
Figure 12:
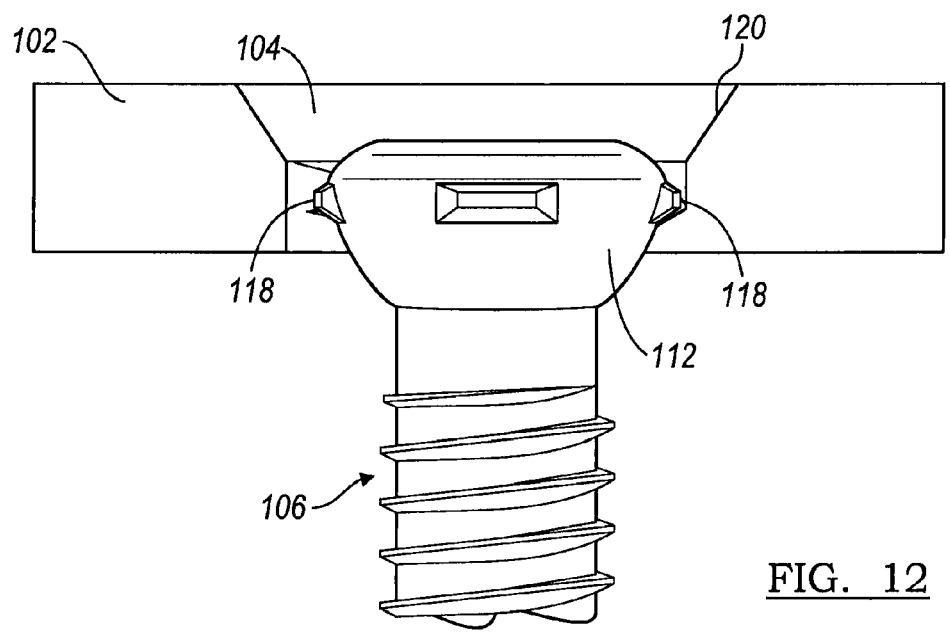

Referring to FIG. 9, the aperture 104 can also include a compression feature 120 for compressing two bones or bone fragments 80 against or closer to each other. The compression feature 120 can be, for example, a compression ramp and/or an elongated slot or extension of the aperture 104. Referring to FIGS. 10-12, an exemplary compression and locking procedure according to the present teachings is illustrated. The locking fastener 106 is inserted into the aperture 104, as shown in FIG. 10. The head 112 of the locking fastener 106 is then rotated using a driver, causing the locking fastener 106 to follow the compression feature 120 and start bone compression, as illustrated in FIG. 11. Further rotation causes the locking fastener 106 to lock relative to the fixation member 102, as illustrated in FIG. 12. It will be understood that, although the locking fastener 106 is illustrated in the exemplary compression procedure, a non-locking faster 108 can also be used to effect bone compression.

The fixation assembly 100 of the present teachings can also be provided as kit including one or more fixation members 102 with different shapes and configuration and/or sizes for the fixation member 102 and the apertures 104 for different applications, different size locking fasteners 106, and different size non-locking fasteners 108. The kit affords the surgeon flexibility to select the appropriate combination of fixation members 102 and locking or non-locking fasteners 106, 108 with or without compression, as needed for a particular procedure. Further, the configuration of the locking mechanism 115 permits easy locking without compression or after compression. The locking mechanism 115 avoids complementary threading between the locking fastener 106 and the aperture 104 of the fixation member 102, and known disadvantages associated with threading, such as spending time and effort for proper alignment for threading and risk of thread failure.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A bone fixation assembly comprising:
a fixation member;
at least one aperture formed through said fixation member;
at least two locking features circumferentially spaced around an inner perimeter of said at least one aperture and including a first end and a second end, said at least two locking features each including a longitudinal axis extending substantially perpendicular to an axis extending through said at least one aperture; and
a fastener received within said at least one aperture and including at least two discrete locking members respectively received in said at least two locking features at said first end, said at least two discrete locking members being circumferentially spaced around an outer perimeter of said fastener, extending from an outer surface of a head of said fastener, and received within said first end in an unlocked state and rotated from said first end to said second end in a locked state to restrict removal of said fastener from said at least one aperture, said at least two locking features respectively engaging said at least two discrete locking members in a direction substantially parallel to said axis extending through said at least one aperture in said locked state.

2. The bone fixation assembly of claim 1, further comprising a ramped surface extending between said first end and said second end of said at least two locking features.

3. The bone fixation assembly of claim 1, wherein said first end of said at least two locking features includes a different radius than said second end of said at least two locking features.

4. The bone fixation assembly of claim 1, wherein said first end of said at least two locking features includes a greater radius than said second end of said at least two locking features.

5. The bone fixation assembly of claim 1, wherein said at least two locking features include a groove receiving a respective one of said at least two discrete locking members therein in said locked state.

6. The bone fixation assembly of claim 5, wherein said groove is disposed proximate to said second end of each of said at least two locking features.

7. The bone fixation assembly of claim 1, wherein said first end is open in a direction substantially parallel to a longitudinal axis of said fastener to receive said at least two discrete locking members in said unlocked state.

8. The bone fixation assembly of claim 1, wherein said first ends of said at least two locking features are disposed substantially in a first plane extending substantially perpendicular to a longitudinal axis of said fastener.

9. The bone fixation assembly of claim 8, wherein said second ends of said at least two locking features are disposed substantially in a second plane extending substantially perpendicular to a longitudinal axis of said fastener.

10. The bone fixation assembly of claim 9, wherein said first plane is offset from said second plane.

11. The bone fixation assembly of claim 1, further comprising a compression feature receiving said fastener and operable to cooperate with said fastener to apply a force to at least one bone in a direction substantially perpendicular to an axis extending through said at least one aperture.

12. The bone fixation assembly of claim 11, wherein said compression feature includes at least one of a ramp and an increased radius portion of said at least one aperture.

13. A bone fixation assembly comprising:
a bone plate for positioning relative to a bone, the bone plate defining an aperture extending therethrough and at least two locking features each having a first end and a second end and a groove having a longitudinal axis formed substantially perpendicular to said axis extending through said aperture; and
a bone fastener rotatable relative to said bone plate and including a shaft extending through said aperture, a head positioned in said aperture, and at least two discrete locking members extending from an outer surface of said head and received in said first end of respective ones of said at least two locking features in a direction substantially parallel to a longitudinal axis of said fastener, said bone fastener and said at least two discrete locking members rotatable relative to said bone plate from said first end to said second end, said second end engaging respective ones of said at least two discrete locking members in a direction substantially parallel to an axis extending through said aperture to secure said bone plate and said fastener to said bone.

14. The bone fixation assembly of claim 13, further comprising a ramp connecting said first end and said second end, said locking members moving from said first end to said second end along said ramp.

15. The bone fixation assembly of claim 13, wherein moving said locking members from said first end to said second end includes moving said fastener further into said bone.

16. The bone fixation assembly of claim 13, wherein said aperture includes at least one of a ramp and an increased radius portion.

17. The bone fixation assembly of claim 16, wherein said at least one of said ramp and said increased radius portion cooperate with said bone fastener to apply a force on said bone in a direction substantially perpendicular to a longitudinal axis of said bone fastener.

18. The bone fixation assembly of claim 17, wherein applying a force on said bone includes engaging said fastener with an inner peripheral surface of said aperture.

* * * * *